US012778579B2

(12) United States Patent
Wahl et al.

(10) Patent No.: US 12,778,579 B2
(45) Date of Patent: Nov. 3, 2026

(54) SUTURE APPARATUS, SYSTEM, AND METHOD

(71) Applicant: A&E Advanced Closure Systems, LLC, Los Angeles, CA (US)

(72) Inventors: Joseph Wahl, Asbury Park, NJ (US); Darren DeMedici, Middletown, NJ (US)

(73) Assignee: A&E Advanced Closure Systems, LLC, Los Angeles, CA (US)

( * ) Notice: Subject to any disclaimer, the term of this patent is extended or adjusted under 35 U.S.C. 154(b) by 140 days.

(21) Appl. No.: 18/557,254

(22) PCT Filed: May 6, 2022

(86) PCT No.: PCT/US2022/028149
§ 371 (c)(1),
(2) Date: Oct. 25, 2023

(87) PCT Pub. No.: WO2022/240692
PCT Pub. Date: Nov. 17, 2022

(65) Prior Publication Data

US 2024/0206871 A1 Jun. 27, 2024

Related U.S. Application Data

(60) Provisional application No. 63/188,755, filed on May 14, 2021.

(51) Int. Cl.
*A61B 17/06* (2006.01)
*A61B 17/84* (2006.01)
(Continued)

(52) U.S. Cl.
CPC .. *A61B 17/06066* (2013.01); *A61B 17/06166* (2013.01); *A61B 17/842* (2013.01);
(Continued)

(58) Field of Classification Search
CPC ... A61B 17/82; A61B 17/823; A61B 17/8004; A61B 17/842; A61B 17/8861;
(Continued)

(56) References Cited

U.S. PATENT DOCUMENTS 1,988,534 A 1/1935 Joseph
2,002,977 A 5/1935 Carr
(Continued)

FOREIGN PATENT DOCUMENTS

AU 743254 1/2002
AU 2017210022 A1 8/2018
(Continued)

OTHER PUBLICATIONS

"U.S. Appl. No. 15/411,682, Examiner Interview Summary mailed Oct. 29, 2018", 3 pgs.
(Continued)

*Primary Examiner* — Katherine H Schwiker
(74) *Attorney, Agent, or Firm* — SCHWEGMAN LUNDBERG & WOESSNER, P.A.

(57) ABSTRACT

A suture apparatus can include a surgical cable having a plurality of woven shape retaining wires. The surgical cable can have a leading end portion and a trailing end portion. The suture apparatus can include a leader connected to the leading end portion of the surgical cable and can be configured to be advanced around bone portions. The woven shape-retaining wires of the cable can be configured to form a twist lock of the surgical cable by twisting of the surgical cable leading and trailing end portions together.

19 Claims, 13 Drawing Sheets

(51) Int. Cl.
*A61B 17/88* (2006.01)
*A61B 17/00* (2006.01)

(52) U.S. Cl.
CPC .................... *A61B 17/8869* (2013.01); *A61B 2017/00836* (2013.01); *A61B 2017/06171* (2013.01)

(58) Field of Classification Search
CPC .......... A61B 17/8869; A61B 17/06166; A61B 17/06; A61B 2017/0496; A61B 2017/06038
See application file for complete search history.

(56) References Cited

U.S. PATENT DOCUMENTS 2,557,877 A 6/1951 Kluson
2,913,015 A * 11/1959 Gerald .................. B65D 63/12 140/118
3,959,960 A 6/1976 Santos
4,050,464 A 9/1977 Hall
4,184,784 A 1/1980 Killian
4,269,180 A 5/1981 Dall et al.
4,327,715 A 5/1982 Corvisier
4,583,541 A 4/1986 Barry
4,959,065 A 9/1990 Arnett et al.
4,966,600 A 10/1990 Songer et al.
5,015,248 A 5/1991 Burstein et al.
5,127,413 A 7/1992 Ebert
5,139,498 A 8/1992 Astudillo Ley
5,312,410 A 5/1994 Miller et al.
5,395,374 A 3/1995 Miller et al.
5,415,658 A 5/1995 Kilpela et al.
5,449,361 A 9/1995 Preissman
5,456,722 A 10/1995 Mcleod et al.
5,514,091 A 5/1996 Yoon
5,522,827 A 6/1996 Combs et al.
5,536,270 A 7/1996 Songer et al.
5,541,380 A 7/1996 Ogden et al.
5,568,865 A 10/1996 Mase et al.
5,569,253 A 10/1996 Farris et al.
5,578,057 A 11/1996 Wenstrom, Jr.
5,643,289 A 7/1997 Sauer et al.
5,649,927 A 7/1997 Kilpela et al.
5,660,091 A 8/1997 Stone et al.
5,702,399 A 12/1997 Kilpeia et al.
5,752,959 A 5/1998 Korhonen
5,755,704 A 5/1998 Lunn
5,810,825 A 9/1998 Huebner
5,830,234 A 11/1998 Wojciechowicz et al.
5,849,012 A 12/1998 Abboudi
5,902,305 A 5/1999 Beger et al.
5,908,421 A 6/1999 Beger
5,935,130 A 8/1999 Kilpela et al.
5,935,133 A 8/1999 Wagner et al.
5,941,881 A 8/1999 Barnes
5,997,542 A 12/1999 Burke
6,017,347 A 1/2000 Huebner et al.
6,077,268 A 6/2000 Farris et al.
6,086,590 A 7/2000 Margulies et al.
6,099,527 A 8/2000 Hochschuler et al.
6,120,506 A 9/2000 Kohrs et al.
6,123,709 A 9/2000 Jones
6,277,120 B1 8/2001 Lawson
6,342,068 B1 1/2002 Thompson
6,378,289 B1 4/2002 Trudeau et al.
6,387,099 B1 5/2002 Lange et al.
6,398,787 B1 6/2002 Itoman
6,399,886 B1 6/2002 Avellanet
6,423,088 B1 7/2002 Fenton, Jr.
6,454,770 B1 9/2002 Klaue
6,475,220 B1 11/2002 Whiteside
6,494,907 B1 12/2002 Bulver
6,520,965 B2 2/2003 Chervitz et al.
6,575,913 B1 6/2003 Woolley
6,605,091 B1 8/2003 Iwanski
6,610,079 B1 8/2003 Li et al.
6,629,975 B1 10/2003 Kilpela et al.
6,730,091 B1 5/2004 Pfefferle et al.
6,832,532 B2 12/2004 Kilpela et al.
6,872,210 B2 3/2005 Hearn
7,052,499 B2 5/2006 Steger et al.
7,156,847 B2 1/2007 Abramson
7,207,993 B1 4/2007 Baldwin et al.
7,229,444 B2 6/2007 Boyd
7,250,054 B2 7/2007 Allen et al.
7,494,461 B2 2/2009 Wells et al.
7,635,365 B2 12/2009 Ellis et al.
7,695,501 B2 4/2010 Ellis et al.
7,785,355 B2 8/2010 Mohr et al.
7,803,176 B2 9/2010 Teague et al.
8,282,675 B2 10/2012 Maguire et al.
8,298,247 B2 10/2012 Sterrett et al.
8,313,517 B2 11/2012 Mohr et al.
8,337,497 B2 12/2012 DesLauriers et al.
8,372,123 B2 2/2013 Smisson et al.
8,460,295 B2 6/2013 McClellan et al.
8,460,345 B2 6/2013 Steger et al.
8,783,671 B2 7/2014 Ranieri et al.
8,840,735 B2 9/2014 Schaffer
8,984,720 B2 3/2015 Gephart
9,265,543 B2 2/2016 Gephart
9,333,021 B2 5/2016 Gephart
9,510,822 B2 12/2016 Poucher et al.
9,510,882 B2 12/2016 Dell'oca
9,561,064 B2 2/2017 Goodwin et al.
10,314,635 B2 6/2019 Gephart
10,405,849 B1 9/2019 Cole et al.
10,426,532 B2 10/2019 Goodwin et al.
10,463,410 B2 11/2019 Goodwin, Jr. et al.
10,485,600 B2 11/2019 Gephart et al.
10,555,729 B1 2/2020 Cole et al.
11,413,077 B2 8/2022 Goodwin, Jr. et al.
2002/0072753 A1 6/2002 Cohen
2002/0177853 A1 11/2002 Chervitz et al.
2002/0177861 A1 11/2002 Sugiyama et al.
2003/0153947 A1 8/2003 Koseki
2004/0138666 A1 7/2004 Fred, IV et al.
2004/0199169 A1 10/2004 Koons et al.
2005/0137624 A1 6/2005 Fallman
2005/0171547 A1 8/2005 Aram
2005/0177179 A1 8/2005 Baynham et al.
2006/0058795 A1 3/2006 Boyd
2006/0089646 A1 4/2006 Bonutti
2006/0155328 A1 7/2006 Foerster
2006/0167464 A1 7/2006 Allen et al.
2006/0271060 A1 11/2006 Gordon
2006/0287653 A1 12/2006 Rhyne
2007/0225715 A1 9/2007 Deffenbaugh et al.
2007/0239209 A1 10/2007 Fallman
2008/0195145 A1 8/2008 Bonutti et al.
2008/0275477 A1 11/2008 Sterrett et al.
2008/0287951 A1 11/2008 Stoneburner et al.
2008/0306553 A1 12/2008 Zucherman et al.
2009/0043316 A1 2/2009 Durgin et al.
2009/0048614 A1 2/2009 Gudladt
2009/0054933 A1 2/2009 Mickiewicz et al.
2009/0069812 A1 3/2009 Gillard et al.
2009/0069851 A1 3/2009 Gillard et al.
2009/0105717 A1 4/2009 Bluechel
2009/0157098 A1 * 6/2009 Meybodi ............ A61B 17/8861 606/139
2009/0171402 A1 7/2009 Dell
2009/0326562 A1 12/2009 White et al.
2010/0042106 A1 2/2010 Bryant et al.
2010/0057091 A1 3/2010 Oosterom
2010/0094294 A1 4/2010 Gillard et al.
2010/0094362 A1 4/2010 Lutze et al.
2010/0121387 A1 5/2010 Belliard
2010/0179595 A1 7/2010 Jackson et al.
2010/0256612 A1 10/2010 Dell
2010/0305571 A1 12/2010 Pratt et al.
2010/0318137 A1 12/2010 Stucki et al.
2010/0331844 A1 12/2010 Ellis et al.
2010/0331892 A1 12/2010 Fell et al.

(56) References Cited

U.S. PATENT DOCUMENTS

| | | | |
|---|---|---|---|
| 2011/0079315 A1 | 4/2011 | Norton et al. | |
| 2011/0112537 A1 | 5/2011 | Bernstein et al. | |
| 2011/0218580 A1 | 9/2011 | Schwager et al. | |
| 2011/0224676 A1 | 9/2011 | Dell | |
| 2011/0319978 A1 | 12/2011 | Schaffer | |
| 2012/0016384 A1 | 1/2012 | Wilke et al. | |
| 2012/0089193 A1 | 4/2012 | Stone et al. | |
| 2012/0109129 A1 | 5/2012 | Bernstein | |
| 2012/0215224 A1 | 8/2012 | Songer | |
| 2012/0226321 A1 | 9/2012 | Gonzalez-hernandez | |
| 2012/0303065 A1 | 11/2012 | Larroque-lahitette et al. | |
| 2013/0116736 A1 | 5/2013 | De Oliveira | |
| 2013/0165933 A1 | 6/2013 | Gephart | |
| 2013/0167334 A1 | 7/2013 | Gephart | |
| 2013/0289564 A1 | 10/2013 | Bernstein et al. | |
| 2013/0331896 A1 | 12/2013 | Holt | |
| 2013/0331897 A1 | 12/2013 | Holt | |
| 2014/0058445 A1 | 2/2014 | Mattchen | |
| 2014/0088688 A1 | 3/2014 | Lilburn et al. | |
| 2014/0142638 A1 | 5/2014 | Goodwin et al. | |
| 2015/0038969 A1 | 2/2015 | Garcia et al. | |
| 2015/0127003 A1 | 5/2015 | Songer et al. | |
| 2015/0182674 A1 | 7/2015 | Schaffer | |
| 2015/0209096 A1 | 7/2015 | Gephart | |
| 2015/0313656 A1 | 11/2015 | Hulliger | |
| 2015/0342654 A1 | 12/2015 | Gephart | |
| 2016/0174997 A1 | 6/2016 | Spitznagel | |
| 2016/0331431 A1 | 11/2016 | Gephart | |
| 2017/0071648 A1 | 3/2017 | Dell'oca | |
| 2017/0143394 A1 | 5/2017 | Goodwin et al. | |
| 2017/0156779 A1 | 6/2017 | Bryant et al. | |
| 2017/0209190 A1 | 7/2017 | Goodwin, Jr. et al. | |
| 2018/0029824 A1 | 2/2018 | Gephart et al. | |
| 2019/0015142 A1 | 1/2019 | Mitchell et al. | |
| 2020/0060737 A1 | 2/2020 | Goodwin, Jr. et al. | |
| 2020/0376646 A1* | 12/2020 | Wink | B25G 1/102 |

FOREIGN PATENT DOCUMENTS

| | | | |
|---|---|---|---|
| CA | 3012198 A1 | 7/2017 |
| CN | 201260694 Y | 6/2009 |
| DE | 7707950 | 7/2026 |
| EP | 0384819 A2 | 8/1990 |
| EP | 1365693 A1 | 12/2003 |
| EP | 3405131 A1 | 11/2018 |
| EP | 4337108 B1 | 9/2025 |
| TW | 314764 U | 9/1997 |
| WO | WO-9318716 A1 | 9/1993 |
| WO | WO-9400063 A1 | 1/1994 |
| WO | WO-9428812 A1 | 12/1994 |
| WO | WO-0149191 A1 | 7/2001 |
| WO | WO-2001049191 A1 | 7/2001 |
| WO | WO-0234120 A2 | 5/2002 |
| WO | WO-2006088452 A2 | 8/2006 |
| WO | WO-2011041624 A2 | 4/2011 |
| WO | WO-2011116364 A1 | 9/2011 |
| WO | WO-2013003719 A1 | 1/2013 |
| WO | WO-2014140100 A2 | 9/2014 |
| WO | WO-2017127692 A1 | 7/2017 |
| WO | WO-2017127714 A1 | 7/2017 |
| WO | WO-2022240692 A1 | 11/2022 |

OTHER PUBLICATIONS

"U.S. Appl. No. 15/411,682, Non Final Office Action mailed Aug. 14, 2018", 15 pgs.
"U.S. Appl. No. 15/411,682, Notice of Allowance mailed Jul. 3, 2019", 5 pgs.
"U.S. Appl. No. 15/411,682, Notice of Allowance mailed Aug. 14, 2019", 2 pgs.
"U.S. Appl. No. 15/411,682, Notice of Allowance mailed Aug. 29, 2019", 2 pgs.
"U.S. Appl. No. 15/411,682, Notice of Allowance mailed Dec. 28, 2018", 5 pgs.
"U.S. Appl. No. 15/411,682, Preliminary Amendment filed Apr. 14, 2017", 3 pgs.
"U.S. Appl. No. 15/411,682, Response filed Nov. 5, 2018 to Non Final Office Action mailed Aug. 14, 2018", 9 pgs.
Et al., "U.S. Appl. No. 15/422,109, filed Feb. 1, 2017", 120 pgs.
"U.S. Appl. No. 16/671,799, Final Office Action mailed Jan. 27, 2022", 10 pgs.
"U.S. Appl. No. 16/671,799, Non Final Office Action mailed Nov. 23, 2021", 11 pgs.
"U.S. Appl. No. 16/671,799, Notice of Allowance mailed Apr. 13, 2022", 8 pgs.
"U.S. Appl. No. 16/671,799, Preliminary Amendment filed Aug. 6, 2021", 6 pgs.
"U.S. Appl. No. 16/671,799, Response filed Jan. 13, 2022 to Non Final Office Action mailed Nov. 23, 2021", 11 pgs.
"U.S. Appl. No. 16/671,799, Response filed Mar. 24, 2022 to Final Office Action mailed Jan. 27, 2022", 10 pgs.
Et al., "U.S. Appl. No. 62/286,062, filed Jan. 22, 2016", 20 pgs.
"U.S. Appl. No. 62/368,753, filed Jul. 29, 2016", 28 pgs.
"Australian Application Serial No. 2017210022, First Examination Report mailed Nov. 19, 2020", 5 pgs.
"Australian Application Serial No. 2017210022, Response filed Apr. 14, 2021 to First Examination Report mailed Nov. 19, 2020", 111 pgs.
"Australian Application Serial No. 2021215153, First Examination Report mailed Sep. 19, 2022", 3 pgs.
"Canadian Application Serial No. 3012198, Office Action Mailed Dec. 23, 2021", 10 pgs.
"Canadian Application Serial No. 3012198, Response Filed Apr. 6, 2022 to Office Action Mailed Dec. 23, 2021", 10 pgs.
"European Application Serial No. 17742033.8, Extended European Search Report mailed Aug. 21, 2019", 7 pgs.
"European Application Serial No. 17742033.8, Response filed Mar. 16, 2020 to Extended European Search Report mailed Aug. 21, 2019", 38 pgs.
"European Application Serial No. 17742033.8, Response to Communication pursuant to Rules 161(1) and 162 EPC filed Feb. 18, 2019", 10 pgs.
Et al., "International Application Serial No. PCT/US2017/014355, filed Jan. 20, 2017", 25 pgs.
"International Application Serial No. PCT/US2017/014355, International Search Report mailed Apr. 14, 2017", 2 pgs.
"International Application Serial No. PCT/US2017/014355, Written Opinion mailed Apr. 14, 2017", 5 pgs.
"International Application Serial No. PCT/US2017/014386, International Preliminary Report on Patentability mailed Feb. 8, 2018", 9 pgs.
"International Application Serial No. PCT/US2017/014386, International Search Report mailed Apr. 14, 2017", 3 pgs.
"International Application Serial No. PCT/US2017/014386, Written Opinion mailed Apr. 14, 2017", 7 pgs.
"International Application Serial No. PCT/US2022/028149, International Search Report mailed Oct. 13, 2022", 7 pgs.
"International Application Serial No. PCT/US2022/028149, Invitation to Pay Additional Fees mailed Aug. 22, 2022", 13 pgs.
"International Application Serial No. PCT/US2022/028149, Written Opinion mailed Oct. 13, 2022", 11 pgs.
"Acute Innovation-Quick and Easy Installation and Re-entry, Acute Innovation", [Online]. Retrieved from the Internet: htto: www.acuteinnovations.com oroducts AcuTie Installtion, (May 16, 2012), 7 pgs.
"Ease of Wire with the Stability of a Plate", AcuTie Sternal Closure System, (Oct. 2010), 12 pgs.
"Re-Entry Options, AcuTie Sternal Closure System", (May 16, 2012), 1 pg.
"Sternalock Blu Primary Closure System, Biomet Microfixation", Form No. BMF00-3265, Rev 05k111 0, (2011), 10 pgs.
"Technique Guide, Modular Sternal Cable System Flexibility and Strength in Sternal Closure and Repair", Synthes CMF, (Jul. 2008), 39 pgs.

(56) References Cited

OTHER PUBLICATIONS

"Technique Guide, Titanium Sternal Fixation System For Stable Internal Fixation of the Sternum", Synthes, Inc., (Oct. 2010), 36 pgs.
"International Application Serial No. PCT US2022 028149, International Preliminary Report on Patentability mailed Nov. 23, 2023", 13 pgs.
"Australian Application Serial No. 2022273598, First Examination Report mailed Aug. 31, 2024", 3 pgs.
"European Application Serial No. 22726230.0, Response filed Jun. 21, 2024 to Communication pursuant to Rules 161(1) and 162 EPC mailed Dec. 21, 2023", 55 pgs.
"Australian Application Serial No. 2022273598, Response filed Dec. 23, 2024 to First Examination Report mailed Aug. 31, 2024", 22 pgs.
"Australian Application Serial No. 2022273598, Subsequent Examination Report mailed Jan. 18, 2025", 2 pgs.
"Canadian Application Serial No. 3,218,217, Response Filed Aug. 29, 2025 to Examiners Rule 86(2) Report mailed Apr. 30, 2025", 35 pgs.

* cited by examiner

SUTURE APPARATUS, SYSTEM, AND METHOD

CLAIM OF PRIORITY

This application is a U.S. National Stage Application under 35 U.S.C. 371 from International Application Serial No. PCT/US2022/028149, filed May 6, 2022, and published as WO 2022/240692 A1 on Nov. 17, 2022, which claims the benefit of U.S. Provisional Patent Application Ser. No. 63/188,755, filed on May 14, 2021, the benefit of priority of which is claimed hereby, and which is incorporated by reference herein in its entirety.

FIELD

This disclosure relates to surgical sutures and, more specifically, to surgical sutures for securing bone portions.

BACKGROUND

A sternotomy may be performed to gain access to the chest cavity of a patient such as during heart surgery and includes cutting the patient's sternum in half. Sternotomy sutures are often used post-sternotomy to lace up or secure the halves of the sternum so that the halves of the sternum will fuse together.

A prior sternotomy suture includes a stainless-steel wire and a needle that is advanced around the cut sternum halves. The needle is cut off from the wire and portions of the wire are twisted together to form a twist-tie. The twisting may be performed by hand or by using a tool to achieve the desired tension in the cable. The twist-tie maintains tension in the wire such that the suture holds the sternum halves tightly together to encourage fusing of the sternum halves.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
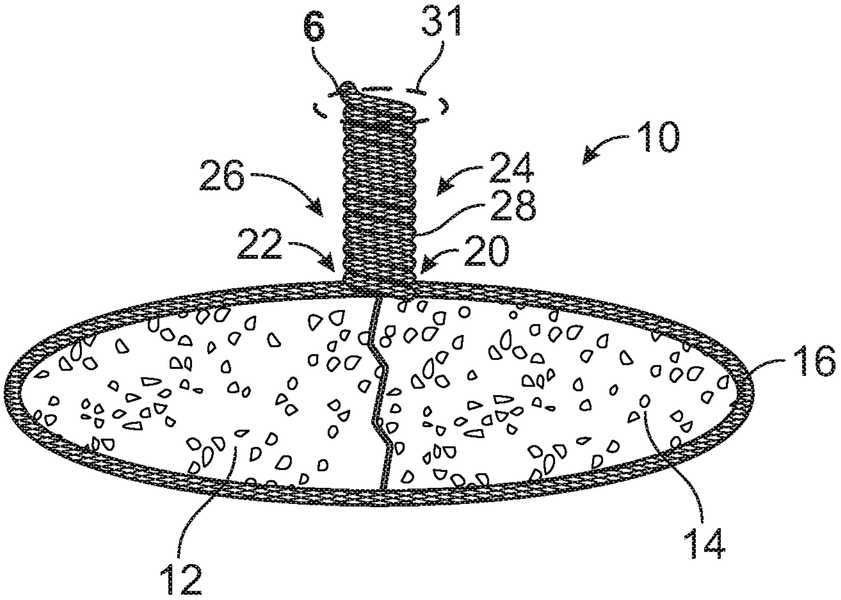
FIG. 1 is an elevational view of a suture having a cable extending around halves of a cut sternum and a twist lock formed by the cable that secures the cable about the sternum.

In accordance with one aspect of the present disclosure, a suture apparatus is provided including a surgical cable having a plurality of woven shape-retaining wires. The surgical cable has a leading end portion and a trailing end portion. The suture apparatus includes a leader connected to the leading end portion of the surgical cable and configured to be advanced around bone portions. The woven shape-retaining wires of the surgical cable are configured to form a twist lock of the surgical cable by twisting of the surgical cable leading and trailing end portions together. In this manner, the surgical cable may be fixed about the bone portions to stabilize the bone portions by twisting the leading and trailing end portions of the cable together. The twist lock thereby provides a secure locking mechanism to hold the cable about the bone portions that may be formed using the cable itself. Further, the woven shape-retaining wires provide a plurality of load-bearing elements to resist separation of the bone portions.

In one form, the woven shape-retaining wires can bite into one another with twisting of the surgical cable leading and trailing end portions and form a mating fit between the twisted wires which resists relative movement of the wires and loosening of twist lock. Further, the woven shape-retaining wires are configured to plastically deform and inhibit loosening of the woven shape-retaining wires. The deformation of the woven shape-retaining wires caused by twisting the leading and trailing end portions imparts residual stress in the wires which fixes the wires in the twisted configuration and resists loosening of the twist lock. The cable may thereby secure itself in position about the bone portions while keeping the bone portion tight and secured together without a crimp or other locking device.

In another aspect, a suture apparatus system is provided and includes a suture apparatus including a surgical cable having a plurality of woven shape-retaining wires. The suture apparatus further includes a leader connected to a leading end portion of the cable and configured to be advanced around bone portions. The suture apparatus system further includes a twister tool having a distal connecting portion configured to be connected to the leading end portion and a trailing end portion of the surgical cable. The twister tool is operable to rotate the distal connecting portion of the twister tool to twist the leading and trailing end portions of the surgical cable connected thereto and cause the woven shape-retaining wires to form a twist lock of the cable. The suture apparatus may thereby be positioned about bone portions and the twister tool utilized to twist the leading and trailing end portions of the surgical cable and cause the woven shape-retaining wires to form a twist-lock of the surgical cable. The twist lock of the surgical cable maintains tension in the surgical cable and secures the surgical cable about the bone portions.

In yet another aspect, a method is provided for stabilizing bone portions. The method includes advancing a leader of a suture apparatus about the bone portions. The suture apparatus includes a surgical cable having a plurality of woven shape-retaining wires, a leading end portion connected to the leader, and a trailing end portion. The method includes connecting the leading and trailing end portions of the surgical cable to a twister tool and forming a twist lock of the cable by using the twister tool to twist the leading and trailing end portions of the surgical cable together. The suture apparatus may thereby be advanced about bone portions, the twister tool connected to the suture apparatus, and the twister tool utilized to form the twist lock of the cable. The method provides a straightforward approach to stabilizing bone portions while providing tensile strength via the woven shape-retaining wires.

The above discussion is intended to provide an overview of subject matter of the present patent application. It is not intended to provide an exclusive or exhaustive explanation of the invention. The description below is included to provide further information about the present patent application.

Figure 3:
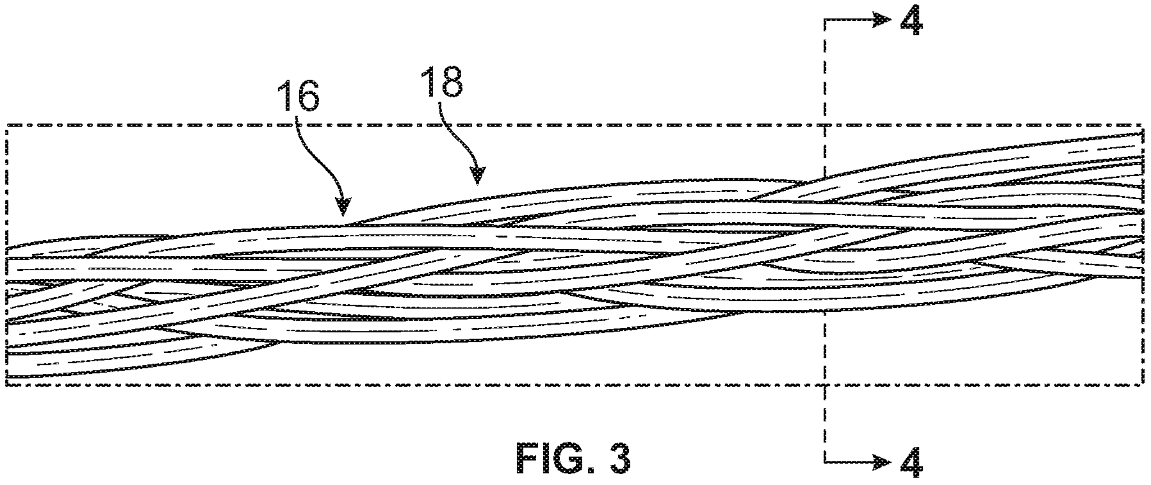
FIG. 3 is an enlarged view of the dashed area in FIG. 2 showing woven wires of a cable of the suture apparatus.

FIG. 1 shows a suture 10 that may be utilized to secure bone portions, such as halves 12, 14 of a cut sternum. The suture 10 includes a cable 16 having a plurality of woven, shape-retaining wires 18 (see FIG. 3). The cable 16 has a leading end portion 20 and a trailing end portion 22 and each of the wires 18 extend the length of the cable 16. The suture 10 includes a twist lock 24 formed by twisting the leading and trailing end portions 20, 22 of the cable 16 together. The twisting of the leading and trailing end portions 20, 22 forms the leading and trailing end portions 20, 22 into intertwined helixes 26 of the leading and trailing end portions 20, 22. The intertwined helixes 26 have a plurality of turns 28 formed by the intertwined leading and trailing end portions 20, 22.

The woven wires 18 of the cable 16 plastically deform with twisting of the leading and trailing end portions 20, 22 into the intertwined helixes 26. As the wires 18 are worked, the wires 18 become more rigid and resist change to their shape. Thus, as the leading and trailing end portions 20, 22 are twisted to form the twist lock 24, each turn 28 of the cable 16 works the lower turns of the cable 16 which further deforms the wires 18 and increases the resistance of the wires 18 to loosening from the tight, intertwined helical shape. Further, the twisting of the leading and trailing end portions 20, 22 also causes the wires 18 to bite or deform into each other with each twist of the twist lock 24 and further resists loosening of the twist lock 24. The wires 18 may bite or deform into each other by, for example, a first wire pressing against a second wire such that an outer surface portion of the first wire deforms an outer surface portion of the second wire. As an example, the wires 18 may each initially have circular cross section perpendicular to the length of the wire. The outer surface portion of the first wire presses against and forms a recess in the outer surface portion of the second wire such that the second wire no longer has a circular cross-section at the outer surface portion. The twisting action urges the outer surface portion of the first wire into the recess of the second wire. Further, the plastic deformation of the wires 18 due to the twisting operation causes the first and second wires to remain in the twisted configuration with the outer surface portion of the first wire engaged with the recess of the outer surface portion of the second wire. The mating or interlocking outer surface portions of the first and second wires 18 further resists relative movement of the first and second wires 18 and further inhibits loosening of the twist lock 24.

As another example, the wires 18 may each initially have circular cross sections and the twisting of the leading and trailing end portions 20, 22 of the cable 16 urges together outer surface portions of first and second wires 18. The outer surface portions of the first and second wires 18 both deform and tightly press against one another. For example, the outer surface portions of the first and second wires 18 may flatten out such that the cross-section of the first and second wires 18 both become non-circular.

In this manner, the deformation of the wires 18 caused by twisting of the leading and trailing end portions 20, 22 rigidly intertwines the wires 18 and forms the twist lock 24. The twist lock 24 fixes the leading and trailing end portions 20, 22 relative to one another and maintains tension in the cable 16, which keeps the sternum halves 12, 14 tightly engaged to facilitate healing of the sternum halves 14, 16.

Figure 15:
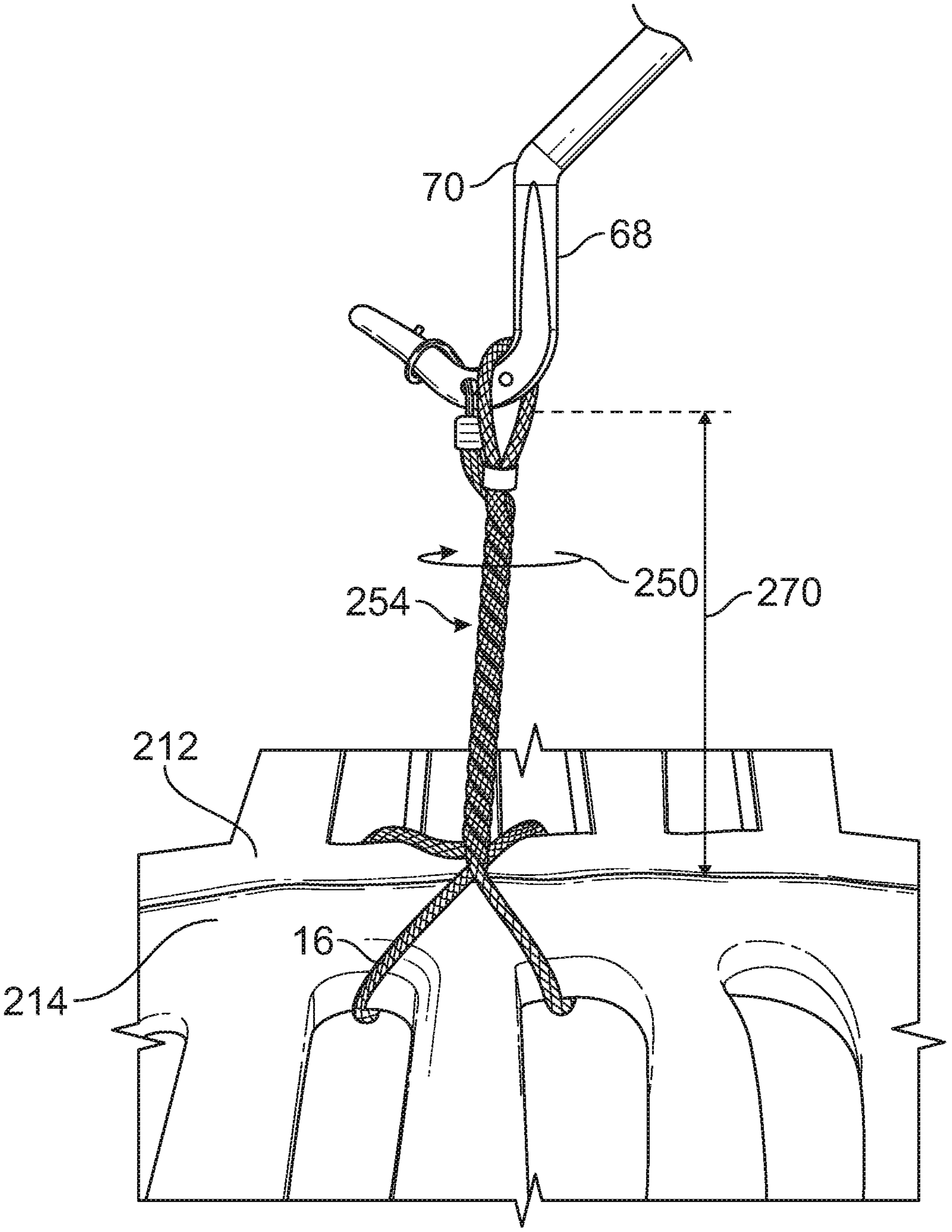
Figure 16:
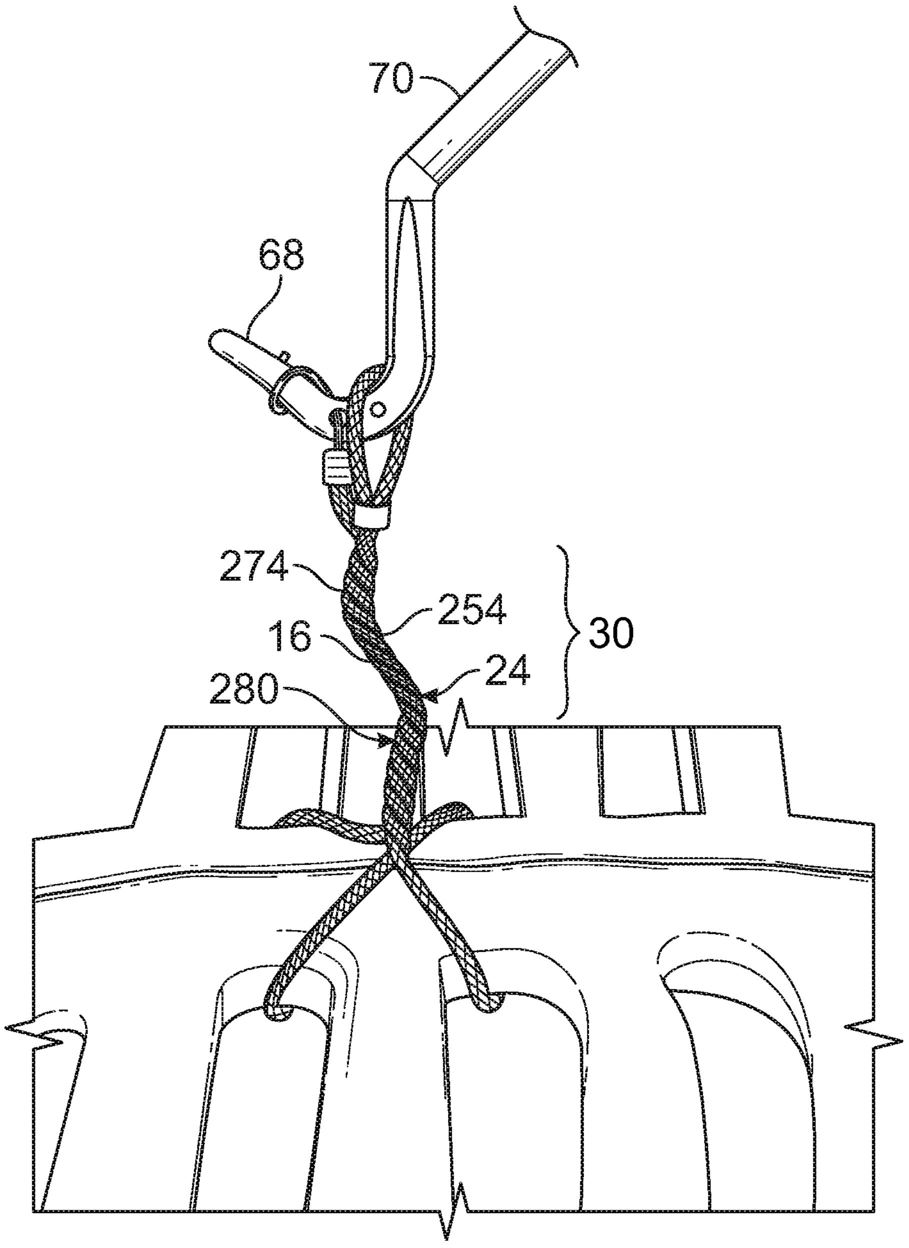
Figure 17:
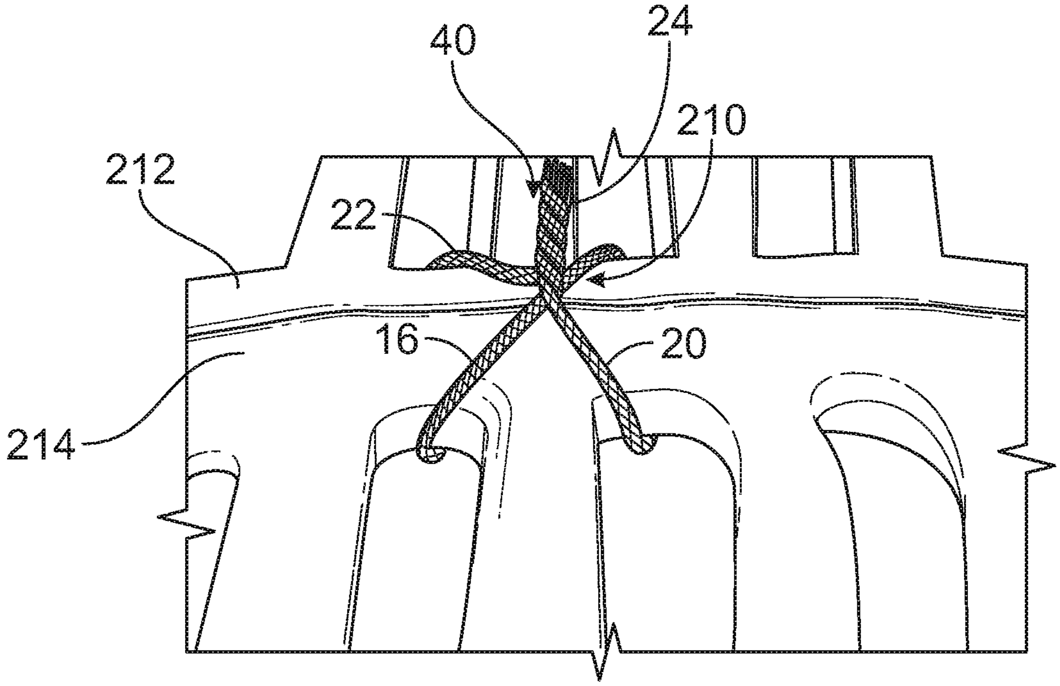

Referring to FIGS. 15-17, to form the twist lock 24, the leading and trailing end portions 20, 22 are twisted using a twister tool 70 to form a cable bundle 254 until double cabling 274 occurs in the cable 16. The double cabling 274 occurs when the cable bundle 254 changes from a single cable bundle into two cable bundles. For example, the double cable 274 may be visually identified when a kinking or a deviation from the straight, column-like arrangement of the cable 16 begins to form as the twister tool 70 twists the leading and trailing end portions 20, 22 of the cable 16. An example of the kinking which forms the double cabling 274 is shown in FIGS. 15 and 16. The double cabling 274 indicates the cable 16 has reached its maximum tension against the sternum halves 12, 14.

Figure 6:
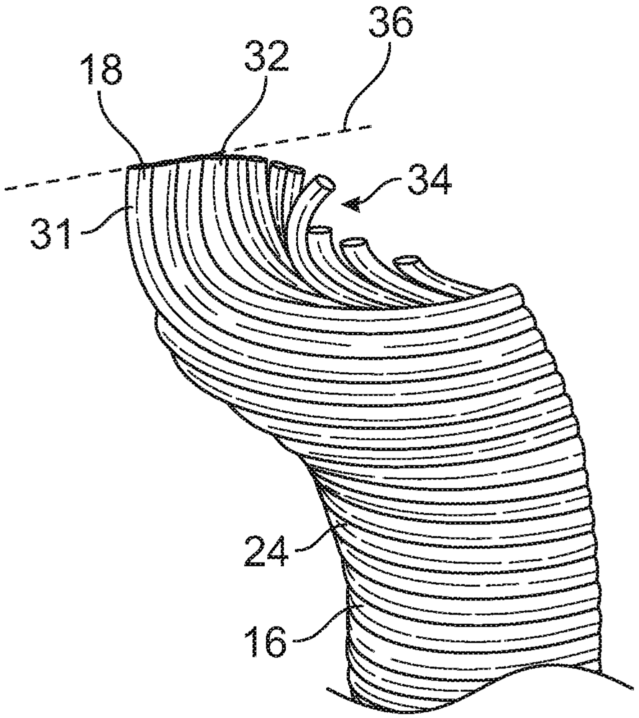
FIG. 6 is an enlarged view of the dashed area of FIG. 1 showing a cut end of the twist lock.

Next, the surgeon may remove an excess portion 30 of the leading and trailing end portions 20, 22 to form a desired length of the twist lock 24. The excess portion 30 is the length of the double cabling 274 beyond the desired length of the twist lock 24. For example, the excess portion 30 may begin a distance in the range of 0.5 inches to 2 inches, such as 1 inch, away from the sternum halves 212, 214. The removing of the excess portion 30 can include cutting leading and trailing end portions 20, 22, such as using diagonal pliers. The cutting operation shears the wires 18 and forms ends 32 (see FIG. 6) of the wires 18 into an end bundle 34. The shearing of the wires 18 further works the material of the wires 18 and introduces residual stress in the wires 18 so that the ends 32 are rigidly held in the end bundle 34 shape. The tightly bundled shape of the wire ends 32 provides a clean end 31 for the twist lock 24 to minimize irritation to surrounding tissues. The surgeon may then bend the twist lock 24 down against the sternum halves 12, 14 to reduce the profile of the twist lock 24 on the sternum halves 12, 14.

Figure 2:
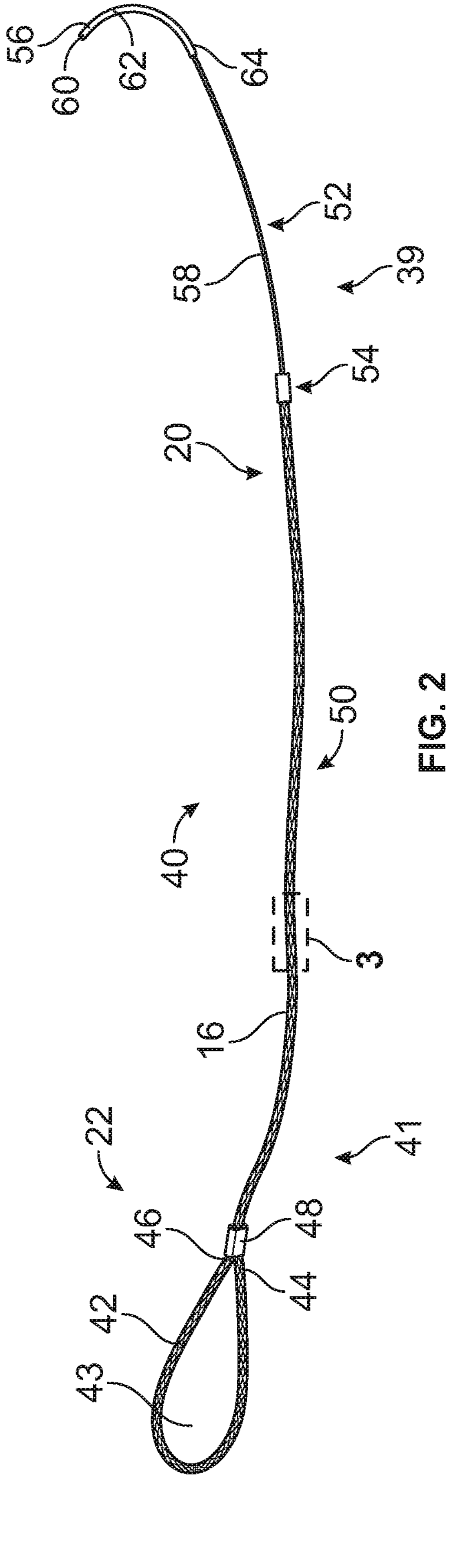
FIG. 2 is a plan view of a suture apparatus used to form the suture of FIG. 1.

In FIG. 2 a suture apparatus 40 is shown as forming the suture 10. The suture apparatus 40 includes the cable 16 having the wires 18 discussed above. In one embodiment, the suture apparatus 40 includes a single cable 16, although in other embodiments two or more cables 16 may be joined together such as by using a crimp.

The suture apparatus 40 has a first end portion 39 that includes the leading end portion 20 of the cable 16 and a second end portion 41 that includes the trailing end portion 22. The second end portion 41 includes a loop 42 formed by a portion 44 of the cable 16 secured to another portion 46 by a connector, such as a crimp 48. The loop 42 forms an opening 43 to receive a hook portion 68 (see FIG. 7) of the twister tool 70 when the twister tool 70 is used to form the twist lock 24 in the cable 16.

The cable 16 includes an intermediate portion 50 between the trailing end portion 22 and the leading end portion 20. The intermediate portion 50 has a length sized to permit a desired shape of the suture 10 to be formed. For example, the suture 10 in FIG. 1 is a single loop suture with the cable 16 looped once around the sternum halves 12, 14. As another example, the intermediate portion 50 may be longer to permit a surgeon to use the suture apparatus 40 to form either the single loop suture of FIG. 1 or a figure-eight suture as in FIG. 17.

The leading end portion 20 of the cable 16 is connected to a leader 52 by a connector, such as a crimp 54. The crimp 54 may be, for example, a swage fitting. The leader 52 is configured to be advanced into a patient's chest cavity, behind the sternum halves, outward from the chest cavity, and moved away from the sternum to pull the leading end portion 20 of cable 16 into the chest cavity, behind the sternum halves, and outward from the chest cavity. The leader 52 may include a needle, such as a curved sternotomy needle 56, and a lead, such as a monofilament lead wire 58. The needle 56 includes a tip 60, a midsection 62, and a butt section 64 secured to the monofilament lead wire 58, such as by a weld. The monofilament lead wire 58 is connected to the leading end portion 20 of the cable 16 by the crimp 54. Alternative or additional approaches may be used to join the monofilament lead wire 58 to the cable 16, such as a weld or an adhesive.

In one embodiment, the leading end portion 20 of the cable 16 includes a length of the cable 16 extending from the crimp 54 toward the loop 42 a first distance that permits the leading end portion 20 to be twisted with the trailing end portion 22. As some examples in this regard, the leading end portion 20 of the cable 16 may extend approximately a half, third, or quarter of the distance between the crimps 48, 54 depending on a particular application. The trailing end portion 22 of the cable 16 may include the loop 42 and a length of the cable 16 extending from the crimp 48 toward the crimp 54 a second distance that permits the trailing end portion 22 to be twisted with the leading end portion 20. As some examples in this regard, the trailing end portion 22 of the cable 16 may extend a half, a third, or a quarter of the distance between the crimps 48, 54 depending on the application. In some embodiments, the trailing end portion 22 does not include the loop 42.

The wires 18 may be made of a plastic or a metallic material, such as stainless steel or titanium. The wires 18 may be annealed to provide the shape-retentive properties of the wires 18. In one embodiment, the wires 18 are of a super annealed metal material. The term super annealed refers to a material that has been annealed until the material is close to the mechanical limits of the material. For example, the wires 18 may be made of super annealed 316L stainless steel. The wires may be annealed until the wires have mechanical properties that satisfy ASTM F1350, which defines the requirements for surgical grade annealed 316 stainless steel.

Figure 4:
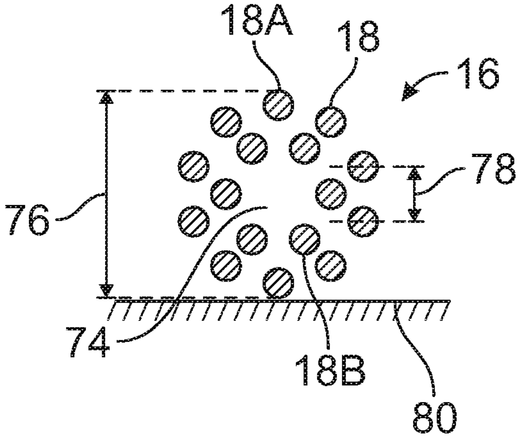
FIG. 4 is a cross-sectional view taken across line 4-4 in FIG. 3 showing the wires of the cable in an initial, untensioned configuration near a surface.

Regarding FIG. 4, in one embodiment the wires 18 are monofilaments woven together with the other wires 18 to form the cable 16. For example, the cable 16 may be a 1×16×0.01 cable, the "1" indicating each wire is woven according to its own pattern, "16" indicating there are 16 total wires in the cable 16, and the "0.01" indicating the diameter of each wire is 0.01 inches. In other embodiments, the cable 16 may include multi-filament micro cables each formed of a plurality of wires 18, the multi-filament micro cables being woven together to form the weave of the cable 16. For example, the cable 16 may be a 2×8×0.01 cable.

In FIG. 4, the wires 18 of the cable 16 include outer wires 18A, inner wires 18B, and an inner space or central void 74. The cable 16 is shown in an initial, untensioned configuration wherein the cable 16 has an effective outer diameter 76 and an effective inner diameter 78. The effective inner diameter 78 may be the distance across the central void 74 the wires 18 naturally assume when the cable 16 is unloaded, such as when the cable 16 is held vertically without tension applied to the cable 16. The wires 18 are loosely woven, meaning that the wires may shift along and about one another as the cable 16 is manipulated. The flexibility of the wires 18 and the ability of the wires 18 to shift along and about one another permits the cable to conform to patient anatomy during positioning and tensioning of the cable 16.

Figure 5:
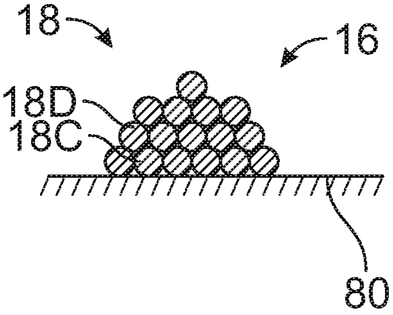
FIG. 5 is a view similar to FIG. 4 showing the wires of the cable under tension and flattened out against the surface.

With reference to FIG. 4, the cable 16 is shown near a surface 80, such as the outer surface of a bone. In FIG. 5, the cable 16 has been tensioned which draws the wires 18 against the surface 80. Further, because the wires 18 are loosely woven, the wires may shift laterally and about each other to have a flattened configuration against the surface 80. In particular, the central void 74 has collapsed and the wires 18 are closely adjacent to each other, such as a layer of wires 18C in contact with the surface 80 and one or more layers of wires 18D on the wires 18C. Because the cable 16 may flatten out against the surface 80, the cable 16 may press against the surface 80 over a larger surface area which keeps the cable 16 from biting into the surface 80. Further, the ability of the individual wires 18 to plastically deform and flatten out permits the cable 16 to be wrapped around patient anatomy at sharper angles than normally permitted using a monofilament surgical wire, such as when forming the figure eight suture of FIG. 17.

Figure 7:
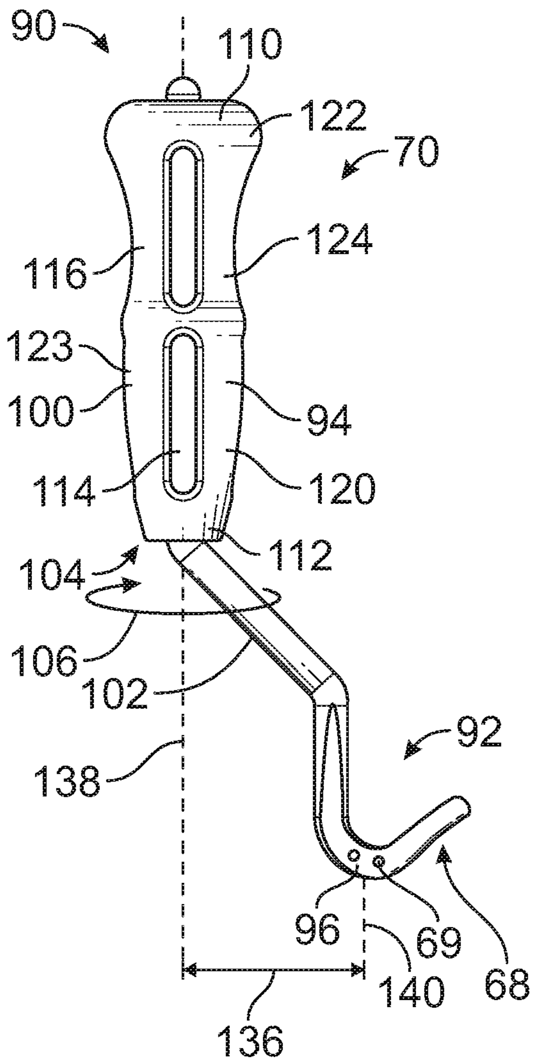
FIG. 7 is a side elevational view of a twister tool that may be connected to the suture apparatus of FIG. 2 after the suture apparatus has been routed around bone portions to twist the cable and form the twist lock.

Regarding FIG. 7, the twister tool 70 includes a proximal end portion 90 and a distal end portion 92. The distal end portion 92 is configured to be connected to the leading and trailing end portions 20, 22 of the cable 16 after the suture apparatus 40 has been advanced around bone portions of a patient lying on an operating table. The surgeon grasps the proximal end portion 90 and moves the twister tool 70 away from the patient, which causes the weight of the patient to remove the slack in the cable 16. The surgeon then moves the proximal end portion 90 in a circular or cranking motion to cause the distal end portion 92 to twist the leading and trailing ends 20, 22 of the cable 16 and tension the cable 16 around the bone portions. This process will be described in greater detail with respect to FIGS. 11-17.

In one embodiment, the proximal end portion 90 of the twister tool 70 includes a handle 94 and the distal end portion 92 includes the hook portion 68 of a support, such as a shaft 102. The leading and trailing end portions 20, 22 of the cable 16 may be connected to the distal end portion 92 of the twister tool 70 by advancing the hook portion 68 through the loop 42 (see FIG. 2) and wrapping the leading end portion 20 and/or monofilament lead wire 58 around the hook portion 68 (see FIG. 12). The twister tool 70 includes a rotary connection 104 between the handle 94 and the shaft 102 that permits the shaft 102 to turn in direction 106 about an axis 138 relative to the handle 94 as the handle 94 is held and moved in a circular motion during twisting of the cable 16, as discussed below.

Regarding FIG. 7, the handle 94 includes a body 100 having a proximal wall 110, a distal wall 112, and through windows or openings 114 formed in a side wall 116 of the handle 94. The handle body 100 has an outer surface 120 and the openings 114 extend radially inward from the outer surface 120 to the shaft 102. To permit the surgeon to maintain a firm grip on the handle 94, the handle 94 has a proximal enlarged portion 122, a narrowed portion 124, and a distal enlarged portion 123. During a twisting operation, the surgeon may grasp the handle 94 with one hand so that the surgeon's index, middle, and thumb fingers are at the narrowed portion 124 and the surgeon's ring and pinky fingers are near the distal enlarged portion 123.

Figure 8:
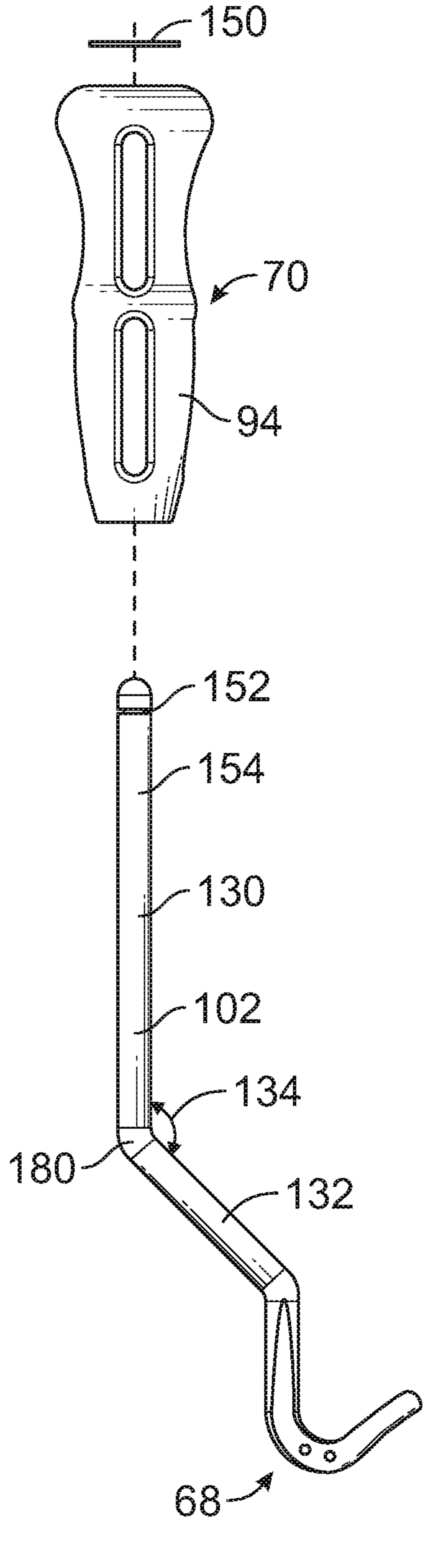
FIG. 8 is an exploded view of the twister tool of FIG. 7 showing a snap ring, a handle, and a shaft with a hook.

With reference to FIGS. 7 and 8, the shaft 102 includes a straight portion 130, an offset portion 132 extending transversely at an angle 134 relative to the straight portion 130, and the hook portion 68. The angle 134 creates an offset distance 136 between a cable-receiving section 96 of the hook portion 68 and the axis of rotation 138 for the shaft 102. The distance 136 creates a moment arm when the hook portion 68 is secured to the suture apparatus 40 (see FIG. 12). The moment arm generally extends from the connection between the suture apparatus 40 and the hook portion cable-receiving section 96 laterally to the axis 138. With this moment arm, the surgeon may turn the handle 94 in a circular motion in a first direction which causes the handle 94 to travel in circle centered on an axis 140 while the hook portion 68, which is generally held at the axis 140 by the connection to the suture apparatus 40, also turns about the axis 140 in the first direction. The force the surgeon imparts to the handle 94 to move the handle 94 in the cranking or circular motions is transferred to the straight portion 130 of the shaft 102. The offset portion 132 extends between the straight portion 130 and the hook portion 68 of the shaft 102 and operates as a moment arm that applies a torque to the hook portion 68 and leading and trailing ends 20, 22 of the cable 16 connected thereto. The torque applied to the hook portion 68 and the cable leading and trailing end portions 20, 22 connected thereto turns the hook portion 68 and the cable leading and trailing end portions 20, 22 about the axis 140. The turning of the hook portion 68 and the cable leading and trailing end portions 20, 22 about the axis 140 twists the leading and trailing end portions 20, 22 of the cable 16.

Regarding FIG. 8, the twister tool 70 includes a retainer to releasably secure the handle 94 to the shaft 102. In one embodiment, the retainer includes a snap ring 150 that engages a groove 152 in an outer surface 154 of the straight portion 130. Regarding FIG. 9, the straight portion 130 extends through an opening 160 in the proximal wall 110 of the handle 94, an opening 162 in an intermediate wall 164 of the handle 94, and an opening 166 of the distal wall 112 of the handle 94. The snap ring 150 is received in a recess 170 of the handle proximal wall 110. The snap ring 150 engages the groove 152 of the shaft 102 and is positioned to contact a surface 172 of the proximal wall 110. The contact between the snap ring 150 and surface 172 resists axial movement of the shaft 102 in direction 174 along the axis of rotation 138. The shaft 102 includes an elbow 180 connecting the straight portion 130 to the offset portion 132. The elbow 180 includes an outer surface 182 that contacts a distal surface 184 of the distal wall 112 to inhibit axial movement of the shaft 102 in direction 186 relative to the handle 94. In this manner, the shaft 102 is rotatably captured in the handle 94.

Figure 9:
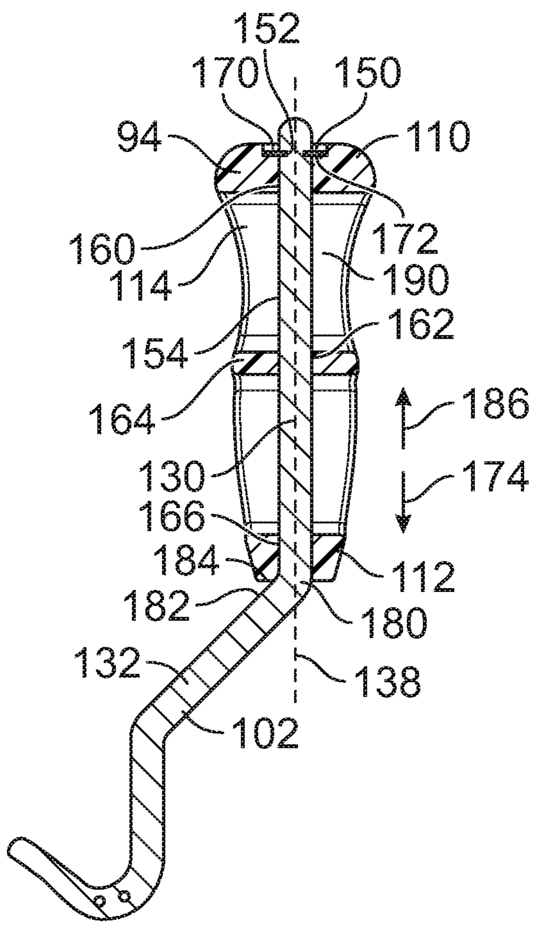
FIG. 9 is a cross-sectional view of the twister tool of FIG. 7 showing the shaft rotatably captured in the handle.

Regarding FIG. 9, the handle 94 facilitates sanitizing of the twister tool 70. More specifically, the twister tool 70 may be sprayed with a solvent to sterilize the twister tool 70. The openings 114 in the handle 94 permit the solvent to travel into the handle 94 and contact the outer surface 154 of the shaft 102 as well as interior surfaces 190 of the handle 94. In some approaches, the twister tool 70 may be disassembled for cleaning. To disassemble the twister tool 70, the snap ring 150 is expanded to disengage one or more projections 200 (see FIG. 10) of the snap ring 150 from the groove 152 of the shaft 102. With the snap ring 150 expanded, the shaft 102 may be removed in direction 174 from the handle 94. The separated handle 94, shaft 102, and snap ring 150 may then be sterilized. In one embodiment, the twister tool 70 is configured to permit some axial movement of the shaft 102 within the handle 94 in directions 186, 174, such as a quarter of an inch, which makes disassembly and assembly of the twister tool 70 easier.

The handle 94 may have a one-piece unitary construction made of a metallic or plastic material. In other embodiments, the handle 94 may be made of two or more components that are assembled. In one embodiment, the shaft 102 has a unitary, one-piece construction. The shaft 102 may be made of a metallic or plastic material, such as stainless steel.

Figure 10:
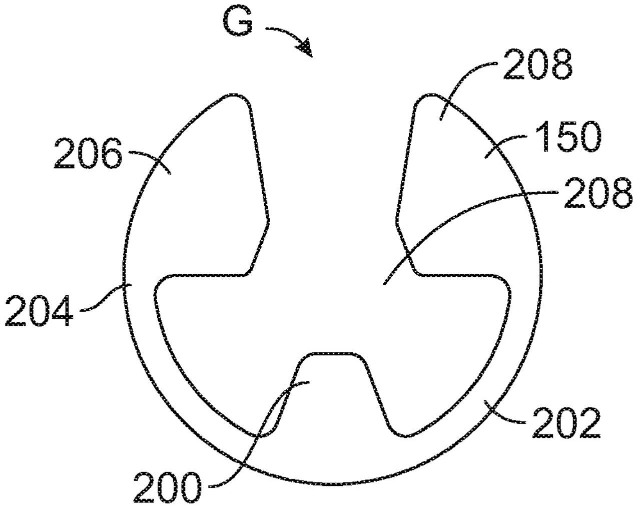
FIG. 10 is a plan view of the snap ring of FIG. 8 showing radial projections of the snap ring that engage a groove of the shaft.
Figure 11:
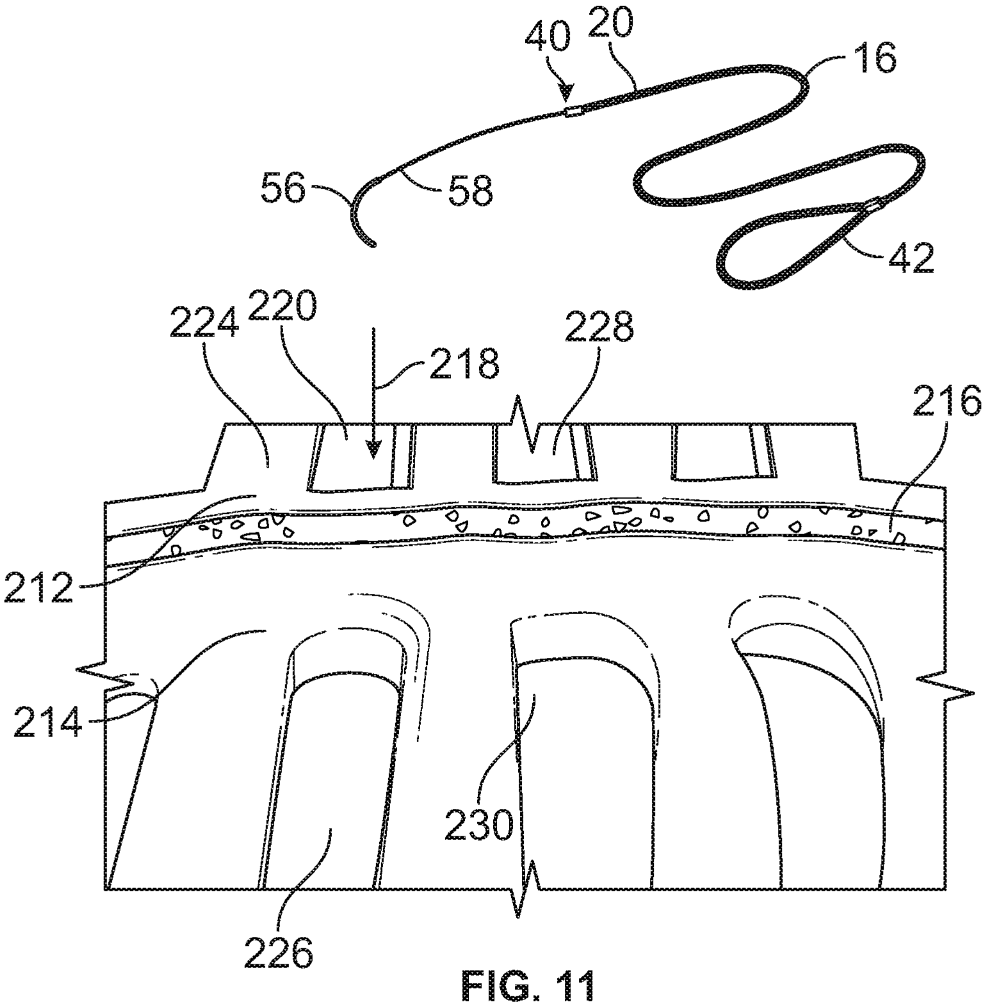
FIGS. 11-17 show a method of forming a figure-eight suture on a cut sternum using the suture apparatus of FIG. 2 and the twister tool of FIG. 7.

Regarding FIG. 10, the snap ring 150 has a body 202 that includes the projections 200 extending radially inward from a peripheral portion 204 of the body 202. The snap ring 150 includes ends 206, 208 that are separated by a gap G. The snap ring 150 has an opening 208 that receives a portion of the shaft 102 therein when the snap ring 150 is engaged with the groove 152 of the shaft 102. The snap ring 150 may be made of a resilient material, such as stainless steel.

With reference to FIGS. 11-17, a method is provided for using the suture apparatus 40 and twister tool 70 to form a suture 210 (see FIG. 17) having a figure-eight pattern 232 (see FIG. 12) to secure sternum halves 212, 214. Regarding FIG. 11, the sternum halves 212, 214 are initially separated by a gap 216, such as due to a surgeon cutting the sternum bone.

Initially, the surgeon routes the suture apparatus 40 around the sternum halves 212, 214 to form a figure-eight shape. This routing includes advancing the needle 56 in downward (with reference to FIG. 11) direction 218 through an intercostal space 220 between ribs 224 of the sternum half 212 and into the patient's chest cavity. The needle 56 is then advanced behind the sternum halves 212, 214 within the chest cavity, upward out of the chest cavity through the intercostal space 226 between ribs of sternum half 214, across the upper surface of the sternum halves 212, 214, back into the chest cavity through an intercostal space 228 of the sternum half 212, behind the sternum halves 212, 214 within the chest cavity, and outwardly through an intercostal space 230 of the sternum half 214. As the needle 56 is advanced about the sternum halves 212, 214, the monofilament lead wire 58 draws the leading end portion 20 of the cable 16 along the path created by the needle 56.

Figure 12:
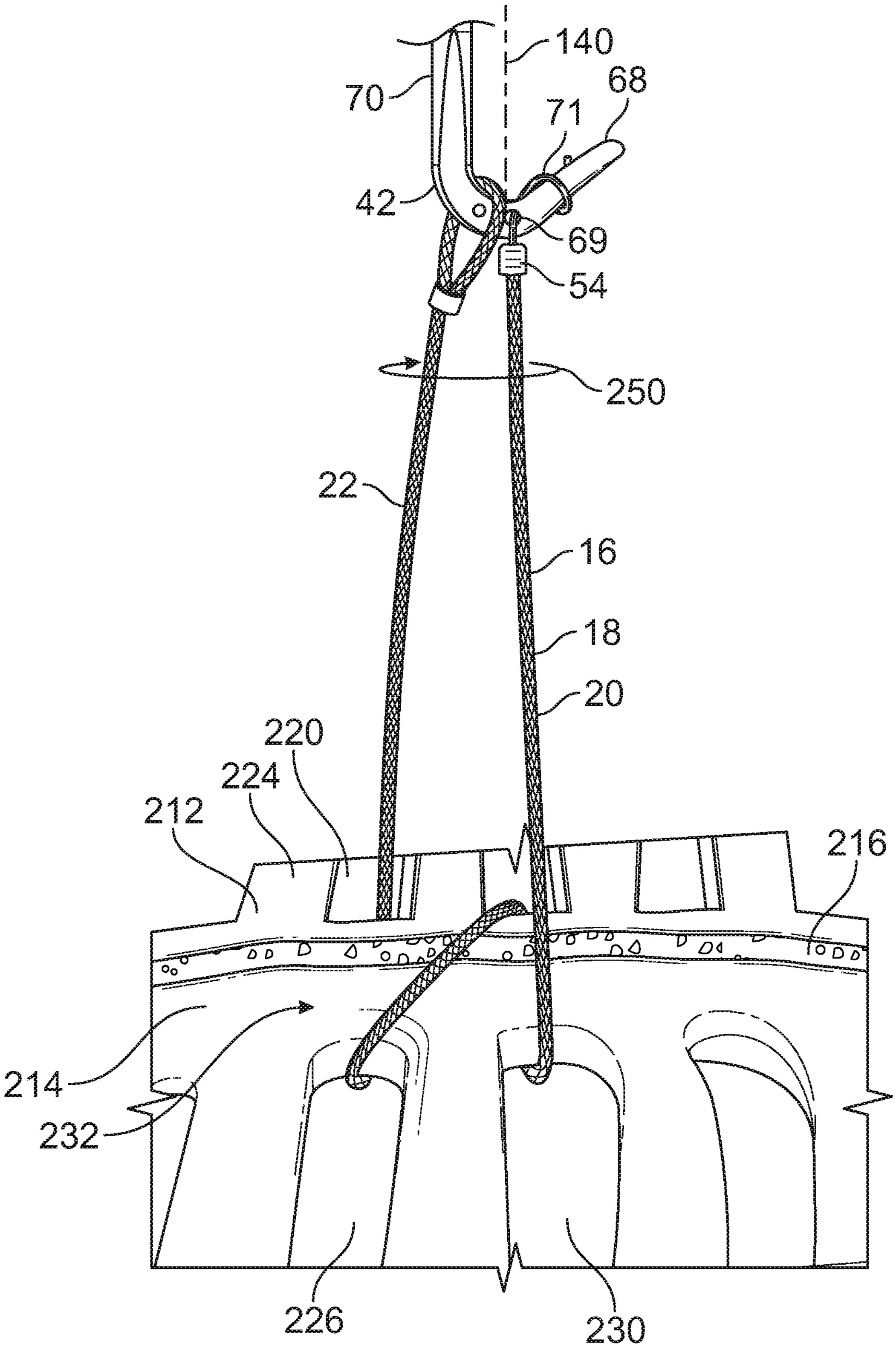

Regarding FIG. 12, the needle 56 and leading end portion 20 of the cable 16 have been advanced about the sternum halves 212, 214 to form the figure-eight pattern 232 about the sternum halves 212, 214. The trailing end portion 22 of the cable 16 extends out of the intercostal space 220 and the leading end portion 20 of the cable 16 extends out of the intercostal space 230.

The method includes connecting the leading and trailing end portions 20, 22 of the cable 16 to the hook portion 68 of the twister tool 70. In one embodiment, the trailing end portion 22 is connected to the hook portion 68 of the twister tool 70 by advancing the hook portion 68 through the loop 42 of the cable 16. The leading end portion 20 is connected to the hook portion 68 by first removing the needle 56 from the monofilament lead wire 58, such as by cutting the monofilament lead wire 58, before advancing a portion 71 of the monofilament lead wire 58 through one of the openings 69 of the hook portion 68. The portion 71 of the monofilament lead wire 58 is advanced away from the hook portion 68 to draw the crimp 54 near the hook portion 68. Next, the portion 71 of the monofilament lead wire 58 extending out of the opening 69 of the hook portion 68 is wrapped around the hook portion 68. In another embodiment, a section of the cable leading end portion 20 is advanced through the opening 69 of the hook portion 68 and the section of the cable leading end portion 20 is wrapped around the hook portion 68.

Regarding FIG. 12, with the leading and trailing end portions 20, 22 of the cable connected to the hook portion 68 of the twister tool 70, the handle 94 of the twister tool 70 is cranked or moved in a circular path in direction 250 about the axis 140. The movement of the handle 94 in direction 250 causes the hook portion 68 of the twister tool 70 to start twisting the leading and trailing end portions 20, 22 of the cable 16 together.

Figure 13:
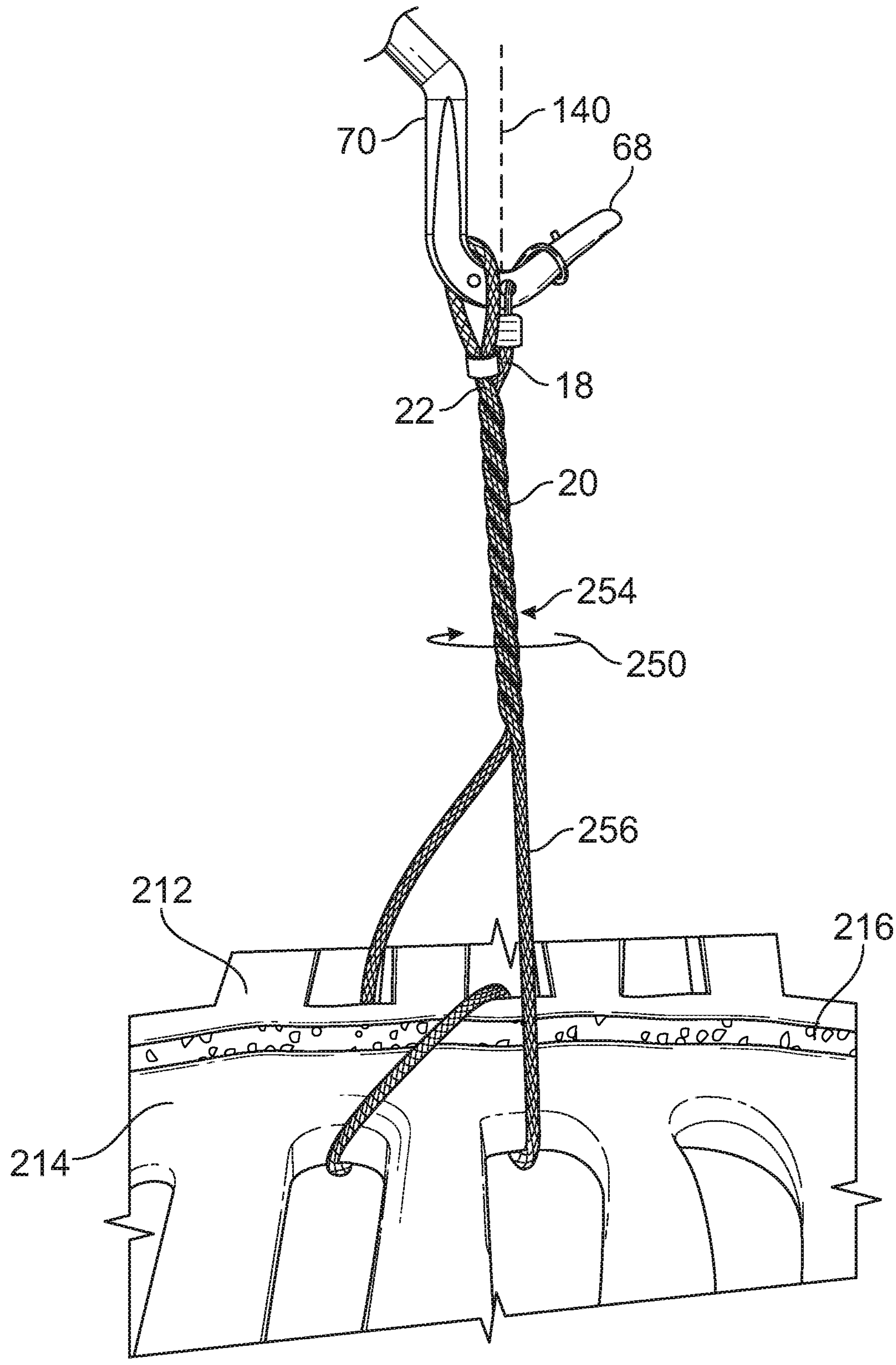

Regarding FIG. 13, the movement of the handle 94 in direction 250 about the axis 140 continues to turn the hook portion 68 in direction 250 and twists the leading and trailing end portions 20, 22 of the wires 18 to form the cable bundle 254 of twisted leading and trailing end portions 20, 22. The cable bundle 254 is initially separated from the sternum halves 212, 214 by straight sections 256 of the cable 16.

Figure 14:
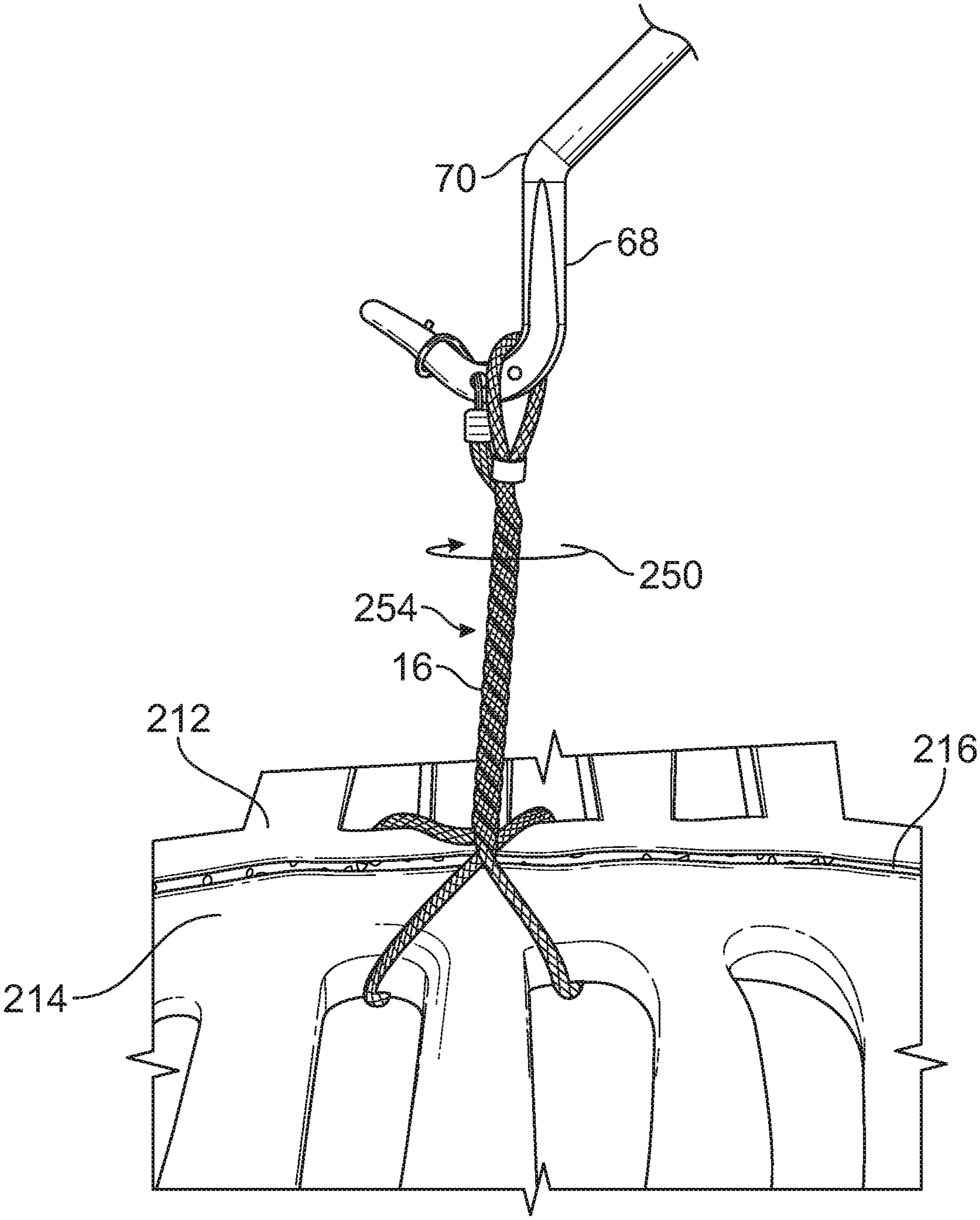

Regarding FIG. 14, the surgeon continues to crank the handle 94 in direction 250 to continue to twist the leading and trailing end portions 20, 22 of the cable 16 together which increases the number of turns of the cable bundle 254 and tightens the turns of the cable bundle 254 until the cable bundle 254 extends all the way from the hook portion 68 to the sternum halves 212, 214. The surgeon may have to rotate the handle 94 several times to twist the cable bundle 254 of FIG. 13 into the form of the cable bundle 254 of FIG. 14.

Comparing FIGS. 14 and 15, the surgeon continues to crank the handle 94 in direction 250 to cause the hook portion 68 to rotate in direction 250. The continued rotation of the hook portion 68 in direction 250 draws more of the cable 16 into the cable bundle 254 and tensions the loops of the cable 16 about the sternum halves 212, 214. The tensioning of the cable 16 urges the sternum halves 212, 214 together and closes the gap 216.

Regarding FIG. 15, the cable bundle 254 has a critical length 270 between the hook portion 68 of the twister tool 70 and the sternum halves 212, 214 wherein the cable bundle 254 extends in a straight column between the hook portion 68 and the sternum halves 212, 214. With the cable bundle 254 having the critical length 270, further cranking of the handle 94 in direction 250 does not substantially increase the compressive force between the sternum halves 212, 214 applied by the cable 16.

Regarding FIG. 16, the method includes further turning or cranking the handle 94 and hook portion 68 in direction 250 until a double cabling 274 occurs in the cable bundle 254. Once the double cabling 274 appears in the cable bundle 254, the surgeon knows that the cable 16 has reached a maximum torque permitted by the cable 16 At this juncture, the wires 18 of the cable 16 have been sufficiently worked or deformed by the twisting operation that the wires 18 will rigidly maintain the intertwined helical configuration of the leading and trailing end portions 20, 22. The surgeon may stop rotating the handle 94 about the axis 252 and form a separation 280 in the cable 16, such as by cutting the cable 16. The surgeon then removes the excess portion 30 of the cable 16, which is still connected to the hook portion 68 of the twister tool 70. The excess portion 30 of the cable 16 may be removed from the hook portion 68 and the twister tool 70 sanitized for use in a subsequent operation.

Regarding FIG. 17, the excess portion 30 of the cable 16 has been removed. The twist lock 24 maintains the tension in the cable 16 of the suture apparatus 210 so that the cable 16 may hold the sternum halves 212, 214 tightly engaged together for healing. The twist lock 24 may be pressed down against the sternum halves 212, 214 to reduce the profile of the twist lock 24.

NOTES AND EXAMPLES

The following, non-limiting examples, detail certain aspects of the present subject matter to solve the challenges and provide the benefits discussed herein, among others.

Example 1 is a suture apparatus comprising: a surgical cable having a plurality of woven shape-retaining wires, the surgical cable having a leading end portion and a trailing end portion; a leader connected to the leading end portion of the surgical cable, the leader configured to be advanced around bone portions; and the woven shape-retaining wires of the surgical cable are configured to form a twist lock of the surgical cable by twisting of the surgical cable leading and trailing end portions together.

In Example 2, the subject matter of Example 1 optionally includes wherein the woven shape-retaining wires include a super annealed, metallic material.

In Example 3, the subject matter of any one or more of Examples 1-2 optionally include wherein the woven shape-retaining wires are configured to plastically deform and inhibit loosening of the woven shape-retaining wires by twisting of the surgical cable leading and trailing end portions together to form the twist lock.

In Example 4, the subject matter of any one or more of Examples 1-3 optionally include wherein the woven shape-retaining wires are each configured to bite into adjacent woven shape-retaining wires and inhibit relative movement between the woven shape-retaining wires by twisting of the surgical cable leading and trailing end portions together to form the twist lock.

In Example 5, the subject matter of any one or more of Examples 1~4 optionally include wherein the woven shape-retaining wires are configured to form a bunched, free end of woven shape-retaining wires upon cutting of the twist lock.

In Example 6, the subject matter of any one or more of Examples 1-5 optionally include wherein the trailing end portion of the surgical cable includes a loop.

In Example 7, the subject matter of any one or more of Examples 1-6 optionally include wherein the leader includes a curved needle.

In Example 8, the subject matter of any one or more of Examples 1-7 optionally include wherein the surgical cable includes a first end at the leading end portion and a second end at the trailing end portion, and wherein the woven shape-retaining wires each extend from the first end to the second end.

In Example 9, the subject matter of any one or more of Examples 1-8 optionally include wherein the woven shape-retaining wires are configured to shift relative to one another and flatten out against the bone portions as the leading and trailing end portions are twisted to form the twist lock.

Example 10 is a suture apparatus system comprising: a suture apparatus comprising: a surgical cable having a plurality of woven shape-retaining wires, the cable having a leading end portion and a trailing end portion; and a leader connected to the leading end portion of the cable and configured to be advanced around bone portions; and a twister tool having a distal connecting portion configured to be connected to the leading and trailing end portion of the surgical cable, the twister tool operable to rotate the distal connecting portion to twist the leading and trailing end portions connected thereto and cause the woven shape-retaining wires to form a twist lock of the cable.

In Example 11, the subject matter of Example 10 optionally includes wherein the woven shape-retaining wires include a super annealed, metallic material.

In Example 12, the subject matter of any one or more of Examples 10-11 optionally include wherein the woven shape-retaining wires are configured to form a bunched, free end of woven shape-retaining wires upon cutting of the twist lock.

In Example 13, the subject matter of any one or more of Examples 10-12 optionally include wherein the trailing end portion of the surgical cable includes a loop and the distal connecting portion includes a hook configured to engage the loop of the surgical cable trailing end portion.

In Example 14, the subject matter of any one or more of Examples 10-13 optionally include wherein the distal connecting portion of the twister tool includes a hook and at least a portion of the leader is configured to be wrapped around the hook.

In Example 15, the subject matter of any one or more of Examples 10-14 optionally include wherein the distal connecting portion of the twister tool includes an opening and at least one of the leader and the leading end portion of the cable is sized to be advanced at least partially through the opening.

In Example 16, the subject matter of any one or more of Examples 10-15 optionally include wherein the twister tool comprises a shaft including the distal connecting portion and a proximal handle rotatably connected to the shaft.

In Example 17, the subject matter of Example 16 optionally includes wherein the shaft extends through at least a portion of the handle, and wherein the handle includes openings that extend inward from an outer surface of the handle to the shaft.

In Example 18, the subject matter of any one or more of Examples 16-17 optionally include wherein the shaft is rotatable relative to the handle about an axis; and wherein the axis is laterally offset from the distal connecting portion of the twister tool.

Example 19 is a method of stabilizing bone portions, the method comprising: advancing a leader of a suture apparatus about the bone portions, the suture apparatus including a surgical cable having a plurality of woven shape-retaining wires, the surgical cable having a leading end portion connected to the leader and a trailing end portion; connecting the leading and trailing end portions of the surgical cable to a twister tool; and forming a twist lock of the cable by using the twister tool to twist the leading and trailing end portions of the surgical cable together.

In Example 20, the subject matter of Example 19 optionally includes wherein forming the twist lock of the cable includes twisting a pair of portions of each of the woven shape-retaining wires into a helical configuration.

In Example 21, the subject matter of any one or more of Examples 19-20 optionally include forming a bunched, free end of the woven shape-retaining wires by cutting the twist lock to length.

In Example 22, the subject matter of any one or more of Examples 19-21 optionally include wherein connecting the leading and trailing end portions of the surgical cable to the twister tool includes advancing a hook of the twister tool through a loop of the suture apparatus.

In Example 23, the subject matter of any one or more of Examples 19-22 optionally include wherein connecting the leading and trailing end portions of the surgical cable to the twister tool includes advancing at least one of the leader and the surgical cable leading end portion through an opening of the twister tool and wrapping the at least one of the leader and the surgical cable leading end portion about the twister tool.

In Example 24, the subject matter of any one or more of Examples 19-23 optionally include wherein forming the twist lock of the surgical cable includes forming a bundle of the surgical cable intermediate the twister tool and the bone portions and twisting the leading and trailing end portions until double cabling begins in the bundle.

In Example 25, the subject matter of any one or more of Examples 19-24 optionally include wherein connecting the leading and trailing end portions of the surgical cable to the twister tool includes connecting the leading and trailing end portions of the surgical cable to a cable-engaging portion of the twister tool, and wherein forming the twist lock of the cable includes rotating the cable-engaging portion of the twister tool while the leading and trailing end portions of the surgical cable are connected to the cable-engaging portion.

In Example 26, the subject matter of any one or more of Examples 19-25 optionally include wherein forming the twist lock of the cable by using the twister tool includes cranking a handle of the twister tool to cause rotation of the leading and trailing end portions of the surgical cable.

In Example 27, the apparatuses or method of any one or any combination of Examples 1-26 can optionally be configured such that all elements or options recited are available to use or select from.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A suture apparatus comprising:

- a surgical cable having a plurality of woven shape-retaining wires, the surgical cable including:
  - a leading end portion including a monofilament;
  - a cable portion including:
    - an intermediate portion including the plurality of woven shape-retaining wires; and
    - a trailing end portion including the plurality of woven shape-retaining wires forming a loop;
  - a first crimp connected to the leading end portion and to the cable portion to secure the leading end portion to the cable portion; and
  - a second crimp connected to the intermediate portion and the trailing end portion to at least partially form the loop;
- a leader connected to the leading end portion of the surgical cable, the leader configured to be advanced around bone portions; and
- wherein the woven shape-retaining wires of the surgical cable are configured to form a twist lock of the surgical cable by twisting of the surgical cable leading end portion and trailing end portion together, and the woven shape-retaining wires are each configured to bite into adjacent woven shape-retaining wires and inhibit relative movement between the woven shape-retaining wires by twisting of the surgical cable leading end portion and trailing end portion together to form the twist lock.

2. The suture apparatus of claim 1, wherein the woven shape-retaining wires include a super annealed, metallic material.

3. The suture apparatus of claim 1 wherein the woven shape-retaining wires are configured to plastically deform and inhibit loosening of the woven shape-retaining wires by twisting of the surgical cable leading and trailing end portions together to form the twist lock.

4. The suture apparatus of claim 1, wherein the woven shape-retaining wires are configured to form a bunched, free end of woven shape-retaining wires upon cutting of the twist lock.

5. The suture apparatus of claim 1, wherein the leader includes a curved needle.

6. The suture apparatus of claim 1, wherein the woven shape-retaining wires are configured to shift relative to one another and flatten out against the bone portions as the leading and trailing end portions are twisted to form the twist lock.

7. The suture apparatus of claim 1, wherein the trailing end portion extends a first distance that is half or less than a second distance between the first crimp and the second crimp.

8. A suture apparatus comprising:

- a surgical cable including a plurality of woven shape-retaining wires, the surgical cable including:
  - a leading end portion including a monofilament;
  - a cable portion including:
    - an intermediate portion including the plurality of woven shape-retaining wires; and
    - a trailing end portion including the plurality of woven shape-retaining wires forming a loop;
  - a first crimp connected to the leading end portion and to the cable portion; and
  - a second crimp connected to the intermediate portion and the trailing end portion to at least partially form the loop;
- a leader connected to the leading end portion, the leader locatable around bone portions;
- wherein the plurality of woven shape-retaining wires are configured to form a twist lock of the surgical cable by twisting of the leading end portion and the trailing end portion together, and the plurality of woven shape-retaining wires are each configured to bite into adjacent woven shape-retaining wires and inhibit relative movement between the plurality of woven shape-retaining wires by twisting of the leading end portion and the trailing end portion together to form the twist lock.

9. The suture apparatus of claim 8, wherein the plurality of woven shape-retaining wires include a super annealed, metallic material.

10. The suture apparatus of claim 8, wherein the plurality of woven shape-retaining wires are configured to plastically deform and inhibit loosening of the plurality of woven shape-retaining wires by twisting of the leading end portion and the trailing end portion together to form the twist lock.

11. The suture apparatus of claim 8, wherein the plurality of woven shape-retaining wires are configured to form a bunched, free end of the plurality of woven shape-retaining wires upon cutting of the twist lock.

12. The suture apparatus of claim 8, wherein the leader includes a curved needle.

13. The suture apparatus of claim 8, wherein the plurality of woven shape-retaining wires are configured to shift relative to one another and flatten out against the bone portions as the leading end portion and the trailing end portion are twisted to form the twist lock.

14. A suture apparatus comprising:

- a surgical cable including a plurality of woven shape-retaining wires, the surgical cable including:
  - a leading end portion including a monofilament;
  - a cable portion including:
    - an intermediate portion including the plurality of woven shape-retaining wires; and
    - a trailing end portion including the plurality of woven shape-retaining wires forming a loop;
  - a first crimp connected to the leading end portion and to the cable portion; and a second crimp connected to the intermediate portion and the trailing end portion to at least partially form the loop, the trailing end portion extending a first distance that is half or less than a second distance between the first crimp and the second crimp;

a leader connected to the leading end portion, the leader locatable around bone portions;

wherein the plurality of woven shape-retaining wires are configured to form a twist lock of the surgical cable by twisting of the leading end portion and the trailing end portion together, and the plurality of woven shape-retaining wires are each configured to bite into adjacent woven shape-retaining wires and inhibit relative movement between the plurality of woven shape-retaining wires by twisting of the leading end portion and the trailing end portion together to form the twist lock.

15. The suture apparatus of claim 14, wherein the plurality of woven shape-retaining wires include a super annealed, metallic material.

16. The suture apparatus of claim 14, wherein the plurality of woven shape-retaining wires are configured to plastically deform and inhibit loosening of the plurality of woven shape-retaining wires by twisting of the leading end portion and the trailing end portion together to form the twist lock.

17. The suture apparatus of claim 14, wherein the plurality of woven shape-retaining wires are configured to form a bunched, free end of the plurality of woven shape-retaining wires upon cutting of the twist lock.

18. The suture apparatus of claim 14, wherein the leader includes a curved needle.

19. The suture apparatus of claim 14, wherein the plurality of woven shape-retaining wires are configured to shift relative to one another and flatten out against the bone portions as the leading end portion and the trailing end portion are twisted to form the twist lock.

* * * * *